United States Patent [19]

Mears

[11] Patent Number: 4,620,533

[45] Date of Patent: Nov. 4, 1986

[54] EXTERNAL BONE FIXATION APPARATUS

[75] Inventor: Dana C. Mears, Oakmont, Pa.

[73] Assignee: Pfizer Hospital Products Group Inc., New York, N.Y.

[21] Appl. No.: 776,259

[22] Filed: Sep. 16, 1985

[51] Int. Cl.[4] ............................................. A61F 5/04
[52] U.S. Cl. ................................ 128/92 Z; 128/92 R
[58] Field of Search .................. 128/92 R, 92 A, 92 E

[56] References Cited

U.S. PATENT DOCUMENTS

| | | | |
|---|---|---|---|
| 2,110,414 | 3/1938 | Bell | 128/92 A |
| 3,809,074 | 5/1974 | De Moude | 128/92 A |
| 4,127,119 | 11/1978 | Kronner | 128/92 A |
| 4,135,505 | 1/1979 | Day | 128/92 A |
| 4,273,116 | 6/1981 | Chicquet | 128/92 A |
| 4,312,336 | 1/1982 | Danieletto et al. | |
| 4,488,542 | 12/1984 | Helland | 128/92 E |

FOREIGN PATENT DOCUMENTS 2033758  5/1980  United Kingdom .

Primary Examiner—Robert Peshock
Assistant Examiner—C. W. Shedd
Attorney, Agent, or Firm—Charles J. Knuth; Peter C. Richardson; Mark Dryer

[57] ABSTRACT

An apparatus for the external fixation and stabilization of a bone fracture comprising fixation pins attached to at least one rigid bar through adjustable clamps which are translatable along said rigid bar wherein the attachment of the pins and bar to the clamps is through articulating balls which allow universal rotational adjustment of each pin or bar. A method for the external fixation and stabilization of a bone fracture utilizing said apparatus is also disclosed.

16 Claims, 18 Drawing Figures

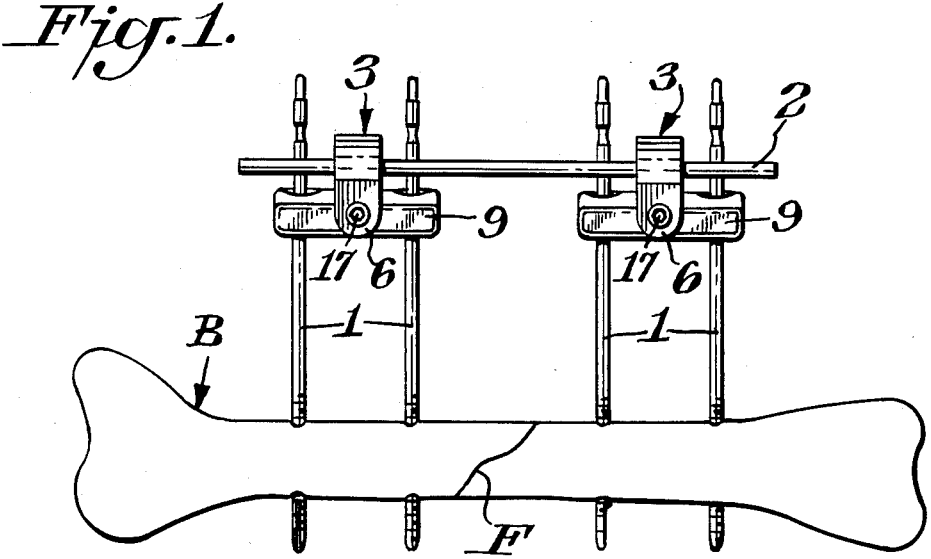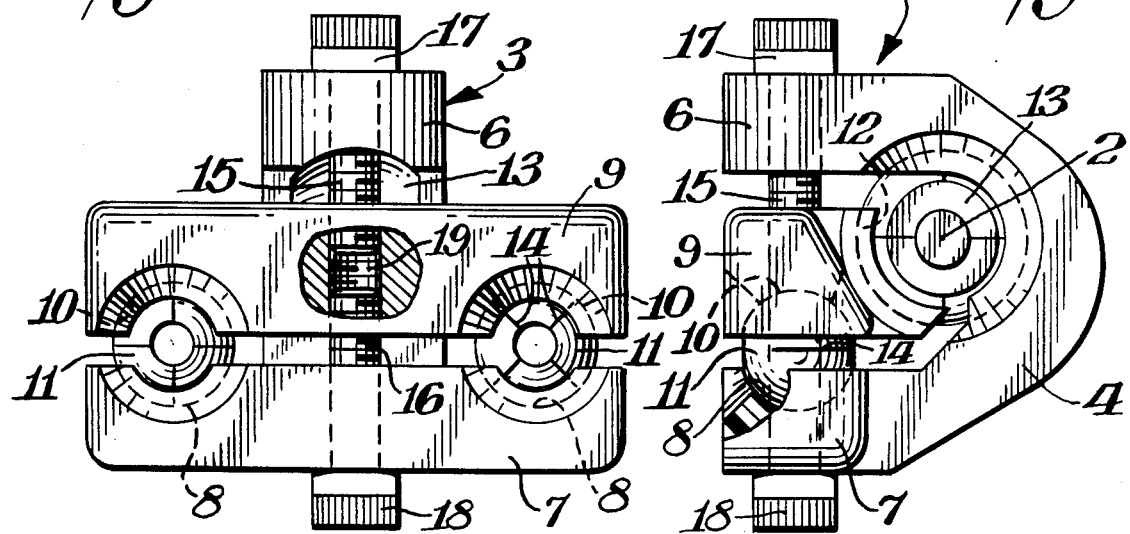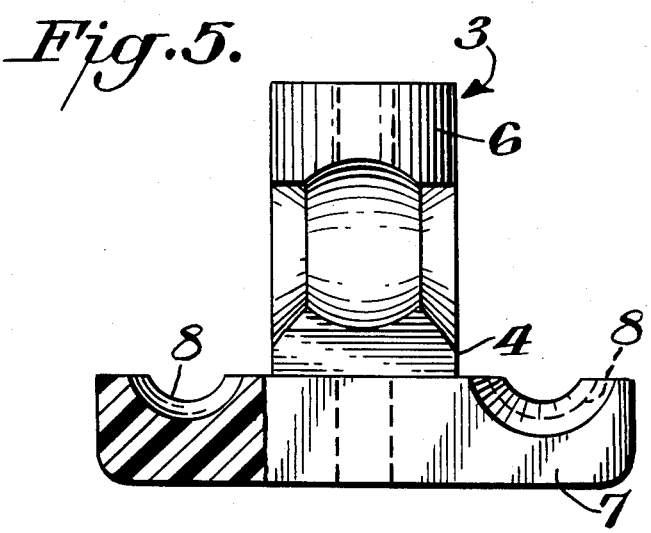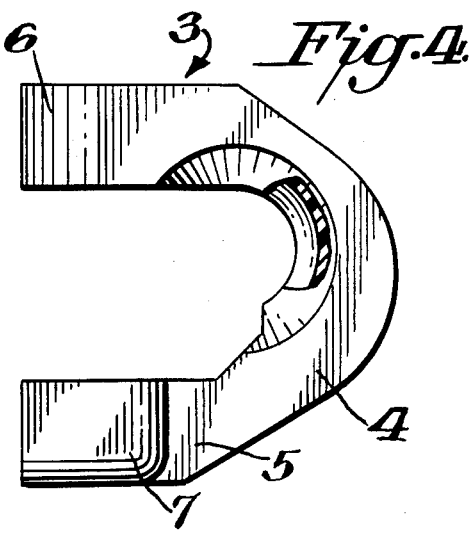

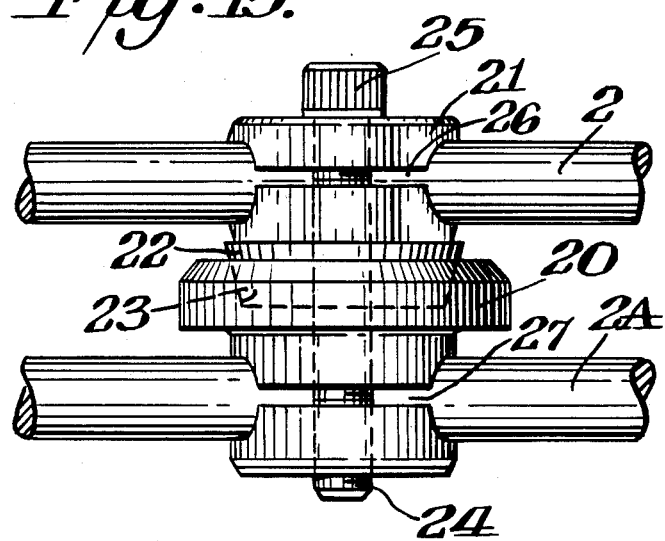
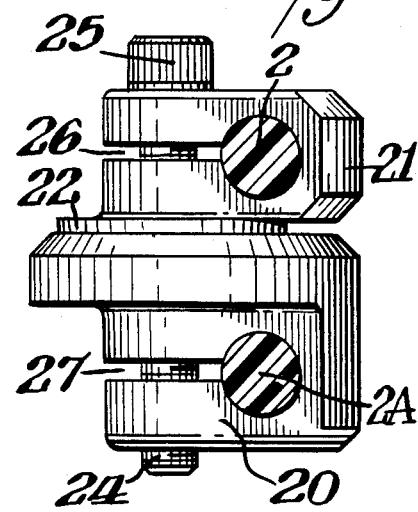
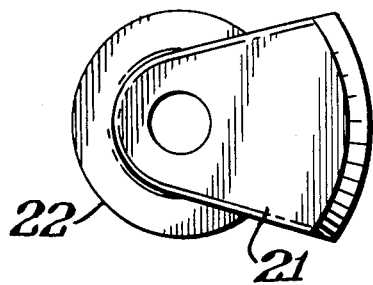
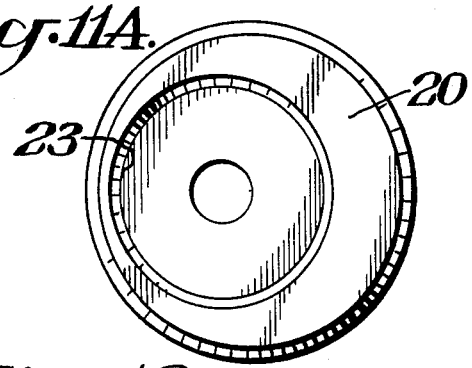
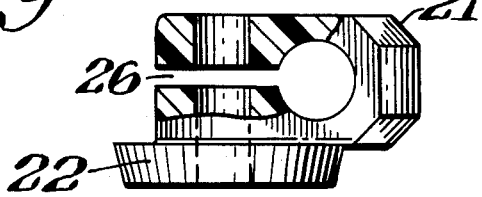
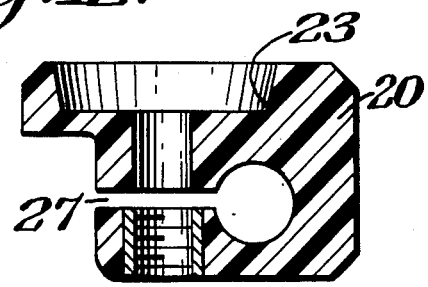
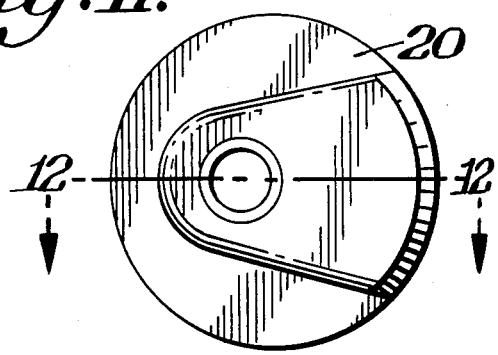

EXTERNAL BONE FIXATION APPARATUS

BACKGROUND OF THE INVENTION

This invention relates to an apparatus for the external fixation and stabilization of a bone fracture. The invention is also concerned with a method for the external fixation and stabilization of a bone fracture utilizing said apparatus.

The setting of fractured bones has been practiced since ancient times and various types of splints and other external fixation devices have been used through the ages. In more recent times, particularly with the advent of X-rays, the art of fixation and stabilization of bone fractures has become more and more precise. Modern devices include surgical pins to hold the bone fragments and various arrangements for clamping or locking the pins to some external bar or framework whereby said bone fragments are held together until the fracture is healed.

One type of apparatus involving pin-holder assemblies is disclosed in U.S. Pat. No. 4,127,119 issued Nov. 28, 1978 to Kronner. The Kronner Circular Compression Frame comprises pins for penetrating bone segments, first and second pin holder assemblies adapted to receive said pins and elongate connector assemblies for coupling said pin holder assemblies.

U.S. Pat. No. 4,312,336 issued Jan. 26, 1982 to Danieletto et al discloses an external axial fixation unit comprising an elongate central body member comprised of two parts adapted to be mutually displaceable parallel to the longitudinal axis of said member and rotatably fixed with respect to each other. The member supports a clamping device for pins adapted to be inserted into a bone segment and the member further includes a pressing and tensioning device. The unit is available commercially under the Trademark Orthofix.

U.S. Pat. No. 4,273,116 issued June 16, 1981 to Claude Chiquet, discloses an external fixation device comprising a plurality of sliding universal articulated couplings for adjustment and locking of connections between pins and tubular tie-rods. Each of said couplings essentially includes a T-shaped member having two arms with longitudinal slots; two nut-and-bolt assemblies disposed in said slots; cooperating clamping means for adjustably clamping pins to said two arms, a spherical adapter sleeve split by staggered slots and slidingly mounted on said tie-rod; a coupling locking clamp and a further nut-and-bolt assembly for securing the device.

The above-described prior art devices are of varying complexity and it has now been found that comparable fixation and stability may be achieved by an apparatus in which the attachment of the bone-piercing pins to the component which establishes fixation and stability is by way of a novel clamp member which allows substantially universal adjustment and fixation of the pins and in which said component is a rigid bar having predetermined torsional, flexural and axial stiffness characteristics, which characteristics may be chosen according to the state of healing of the fracture.

Additional stabilization may be achieved by the addition of one or more further rigid bars, each of said bars being attached to each other bar by a novel clamp comprising two separatable portions adjustably connected to each other through a taper lock.

In an alternative embodiment of the invention said taper lock clamp may be used to couple a pin to a rigid bar as part of a modified apparatus comprising a plurality of such couplings.

SUMMARY OF THE INVENTION

In accordance with the present invention there is provided an apparatus for the external fixation and stabilization of a bone fracture, which comprises at least two pins adapted to pass through skin, flesh and bone on opposite sides of the fracture site; at least one first rigid bar having predetermined torsional, flexural and axial stiffness characteristics; at least two pin-to-bar clamps, each connecting at least one of said pins to said bar in a manner such that said clamps are translatable along said bar, the attachment of each of the pins to its associated clamp and of the bar to each clamp being each through an articulating ball which allows universal rotational adjustment of the pin or bar, respectively, each of said clamps comprising a body portion with a first branch connected to a second branch, an arm located at the terminus of said first branch, said arm extending perpendicularly to the plane of the body portion and having at least one indent, and a capture bar overlying said extending arm, wherein the branches of said body portion embrace the articulating ball which accommodates said rigid bar and the capture bar is provided with at least one indent which is juxtaposed to said indent in said extending arm so that said indents cooperate to accommodate each articulating ball holding a pin; and locking means for locking each pin to each clamp and each clamp to said rigid bar.

Preferably, said body portion of each pin-to-bar clamp is substantially C-shaped, said capture bar is located between the branches thereof with one end extending towards the crook of the C, and said end and said branches cooperate to embrace the articulating ball which accommodates said rigid bar.

The invention also provides an apparatus for the external fixation and enhanced stabilization of a bone fracture, which comprises at least two pins adapted to pass through skin, flesh and bone on opposite sides of the fracture site; at least one first rigid bar having predetermined torsional, flexural and axial stiffness characteristics; at least one second rigid bar having similar characteristics to said at least one first rigid bar; at least two pin-to-bar clamps and at least one bar-to-bar clamp, each of said pin-to-bar clamps connecting at least one of said pins to one of said rigid bars in a manner such that said clamps are translatable along said bar or bars, the attachment of each of the pins to its associated pin-to-bar and of each bar to each pin-to-bar clamps being through an articulating ball which allows universal rotational adjustment of the pin or bar, respectively; each of said pin-to-bar clamps comprising a body portion with a first branch connected to a second branch and having an arm located at the terminus of said first branch, said arm extending perpendicularly to the plane of the body portion and having at least one indent; and a capture bar overlying said extending arm, wherein the branches of said body portion embrace the articulating ball which accommodates a rigid bar and the capture bar is provided with at least one indent which is juxtaposed to said indent in said extending arm so that said indents cooperate to accommodate each articulating ball holding a pin; and locking means for locking each pin to each pin-to-bar clamp and each pin-to-bar clamp to each rigid bar; each of said bar-to-bar clamps comprising two separable portions adjustably connected to each other through a taper lock.

The invention further provides a modified apparatus for the external fixation and stabilization of a bone fracture, which comprises at least two pins and at least one rigid bar as described above, wherein at least one of the pins is coupled to a rigid bar through a clamp comprising two separable portions adjustably connected to each other through a taper lock. The resulting pin-to-bar coupling is used together with one or more similar couplings and/or together with one or more pin-to-bar arrangements as described above to provide the final desired fixation apparatus.

The invention still further provides a method for the external fixation and stabilization of a bone fracture which comprises drilling at least one hole through the skin, flesh and bone on opposite sides of the fracture site, fixing a pin in each of said holes, each of said pins being attached, through an articulating ball located in a clamp to at least one first rigid bar, said bar being attached to each of said clamps through an articulating ball, each of said clamps comprising a body portion with a first branch connected to a second branch and having an arm with at least one indent at the terminus of said first branch, said arm extending perpendicularly to the plane of the body portion and a capture bar overlying said extending arm, wherein the branches of said body portion embrace the articulating ball which accommodates said rigid bar and the capture bar is provided with at least one indent which is juxtaposed to said indent in said extending arm so that said indents cooperate to accommodate each articulating ball holding a pin; adjusting the position of the pins both rotationally and linearly along the first rigid bar to ensure correct alignment of the pins and bar relative to the fracture and locking the pins and bar in said correct alignment by locking means associated with each clamp.

DETAILED DESCRIPTION OF THE INVENTION

The apparatus according to the invention includes novel pin-to-bar clamps which enable external fixation and stabilization of a bone fracture to be achieved in a simple and expeditious manner. Moreover, positioning of the pins is extensively adjustable and locking of the apparatus once the desired optimum position is attained is very simple.

The pin-to-bar clamps, which are an essential feature of the apparatus, may be of any configuration consistent with the description set out above but a preferred embodiment of the invention is an apparatus in which each pin-to-bar clamp is substantially C-shaped and the invention will be particularly described with reference to this preferred embodiment.

In the preferred embodiment wherein the clamp is substantially C-shaped, the captive bar is located between the branches thereof with one end extending towards the crook of the C, and said end and said branches cooperate to embrace the articulating ball which accommodates the rigid bar.

In such an embodiment the locking means preferably comprises a first locking means for locking each pin to each clamp and independent second locking means for locking each clamp to said rigid bar.

In a particularly preferred embodiment the capture bar is provided with at least one first threaded socket on one side and a second threaded socket on the opposite side, said first locking means is at least one screw which passes through said extending arm and engages with said first threaded socket and said second locking means is a screw which passes through the second branch of the body portion and engages with said second threaded socket.

The preferred embodiment of the invention also comprises four pins arranged in two pairs, each pair attached to a single clamp, wherein the extending arm of each clamp extends on both sides of the first branch of the body portion.

It is particularly preferred in the apparatus of the invention that said first rigid bar and said clamps, apart from metallic inserts, are made from X-ray translucent material. This feature enables the healing progress of the fracture to be determined by X-ray examination without the necessity of removing or altering the position of the fixation apparatus to completely observe the fracture site. This is particularly advantageous in the case of a compound fracture or a multiple break.

Preferably the X-ray translucent material of said bar is an epoxy/carbon or epoxy/fiberglass composite, and the X-ray translucent material of said clamps is a nylon/carbon fiber composite.

Another advantage of using a material such as epoxy/carbon or epoxy/fiberglass composite for the rigid bar is that such material may be obtained with varying torsional, flexural and axial stiffness characteristics. By changing the bars from very rigid to less rigid during the healing of the fracture the course of the healing and strengthening of the bone is improved.

Accordingly, in a preferred embodiment of the invention said first rigid bar is one of a series of bars each made from a material having different torsional, flexural and axial stiffness characteristics from those of other members of the series, said bars being adapted to be interchanged in the apparatus to provide external fixation of diminishing stiffness as the healing of the fracture to which the apparatus is applied progresses.

Additional stabilization may be achieved by the use of a combination of at least two rigid bars so that the apparatus comprises a framework of said bars cooperating with each other to provide the desired stabilization. In accordance with this embodiment there is provided an apparatus as described above which additionally includes at least one second rigid bar operatively attached to said first rigid bar through a bar-to-bar clamp comprising two separable portions adjustably connected to each other through a taper lock.

Preferably said taper lock comprises a first substantially U-shaped member adapted to accommodate a first rigid bar within an aperture formed by the opposing legs of the U and located at the distal end of the member and having a male-tapered portion attached to the outside surface of one of the legs; a separate second substantially U-shaped member adapted to accommodate a second rigid bar in a manner similar to said first member, said second member having a female-tapered portion attached to the outside surface of one of its legs; said male and female tapered portions being adapted to co-operatively engage with each other; and locking means for locking said portions and said bars in a desired operative engagement with each other.

In an alternative embodiment of the invention, a taper lock clamp as described above may be used to couple a pin to a bar and a modified apparatus comprising two or more such couplings or a combination of one or more of such couplings with a pin-to-bar assembly as described above may be used as a fixation apparatus according to the invention.

A preferred form of the embodiment which includes at least one second rigid bar is an apparatus comprising at least two first rigid bars, each attached through said pin-to-bar clamps to at least two pins adapted to be affixed on opposite sides of said fracture site, with each pair of pins at an angle to the plane of each other pair of pins, said rigid bars being connected through bar-to-bar clamps to at least one second rigid bar in a manner such that the arrangement of first and second rigid bars forms a framework providing enhanced stability to the fractured bone.

Also, it is a preferred feature of this embodiment that each rigid bar and each clamp, apart from metallic inserts, is made from X-ray translucent material; and it is particularly preferred that the X-ray translucent material of said bars is an epoxy/carbon or epoxy/fiberglass composite, and the X-ray translucent material of said clamps is a nylon/carbon fiber composite.

Further advantages are achieved, as described above, when this embodiment is one in which each first rigid bar is one of a series of bars each made from a material having different torsional, flexural and axial stiffness characteristics from those of other members of the series, said bars being adapted to be interchanged in the apparatus to provide external fixation of diminishing stiffness as the healing of the fracture to which the apparatus is applied progresses.

The apparatus according to the invention provides improved external fixation and stabilization of a bone fracture when it applied about the site of the fracture in accordance with the method described above and the fracture may be further stabilized by the inclusion of at lest one second rigid bar operatively attached to said first rigid bar through a clamp comprising two separable portions adjustably connected to each other through a taper lock.

DESCRIPTION OF THE DRAWINGS

Preferred embodiments of the invention are illustrated in the accompanying drawings, in which:

FIG. 1 is a side view of a preferred embodiment affixed to bone;

FIG. 2 is a side view of a pin-to-bar clamp used in the embodiment of FIG. 1;

FIG. 3 is an end view of the pin-to-bar clamp of FIG. 2;

FIG. 4 is a side view of the substantially C-shaped body portion of said pin-to-bar clamp;

FIG. 5 is an end view of said body portion;

FIG. 10 is a side view of a bar-to-bar clamp;

FIG. 11 is a bottom plan view of the female component of said bar-to-bar clamp;

FIG. 11A is a top plan view of said female component.

FIG. 12 is a section through 12—12 of FIG. 11;

FIG. 13 is a plan view of the male component of said bar-to-bar clamp;

FIG. 14 is a side view of said male component;

FIG. 15 is an end view of a bar-to-bar clamp with two bars placed therein.

Referring to FIG. 1 of the drawings, a bone B having a fracture F is stabilized by the application of a preferred embodiment of the invention which comprises four pins 1 inserted into holes drilled in the bone, two on each side of the site of the fractue. Each of the pins is preferably a standard 3 mm. or 5 mm. diameter half or transfixing pin. The pin may be made of stainless steel or any other suitable material, for example, titanium or graphite composite. It is preferred that the pins are applied with the aid of predrilling guides which are provided with the apparatus of the invention and allow for predrillling and proper placement of the pins. This procedure preferably will be performed through sleeves, thereby protecting the surrounding soft tissue.

Figure 6:
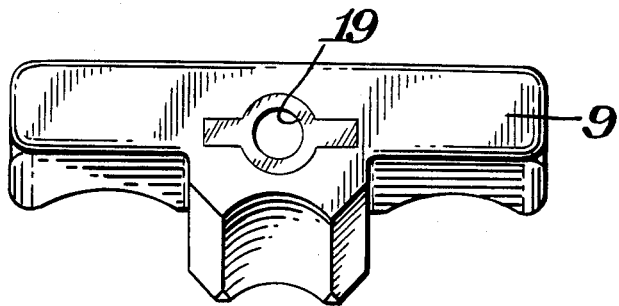
FIG. 6 is a top plan view of a capture bar of the clamp of FIGS. 2 and 3.
Figure 8:
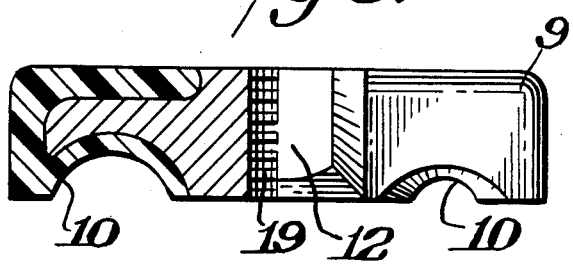
FIG. 8 is a side view, partially in cross-section of said capture bar.
Figure 8A:
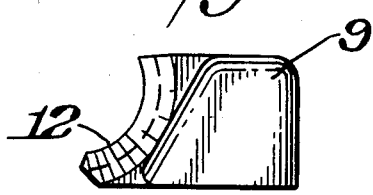
FIG. 8A is an end view of said capture bar.
Figure 7:
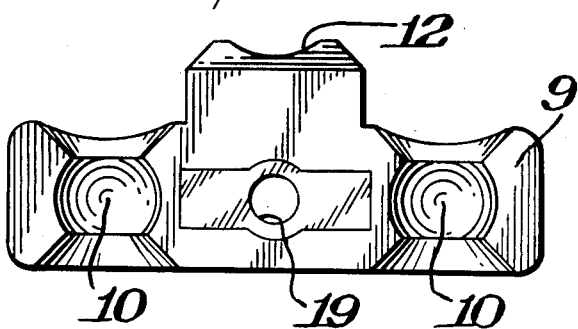
FIG. 7 is a bottom plan view of said capture bar.

Each of said pins is adjustably attached to a rigid bar 2 through pin-to-bar clamps 3.

The rigid bar, which provides the supporting link between the various clamps and thereby stability to the fixation system, is preferably a solid circular cross-section bar of either 8 mm. or 5 mm. diameter. The length of the bar will depend upon the size of the bone to be stabilized and the invention includes within its scope bars of various lengths. The bar may be made of any suitable material possessing the desired rigidity. While stainless steel is a suitable material, it is particularly preferred that the rigid bar be made of X-ray translucent material. This provides the advantage that X-ray examination of the fracture may be conducted from any angle without the necessity of removing or altering the position of the fixation apparatus. Preferred X-ray translucent materials are epoxy/carbon fiber or epoxy/fiberglass composites. Additionally the rigid bar preferably is chosen from a series of bars each made from a material having different torsional, flexural and axial stiffness characteristics from those of other members of the series, so that external fixation of diminishing stiffness may be provided by interchanging the rigid bar for one of less rigidity as the healing of the fracture progresses. In such a series the most rigid bar of the series may be a bar made from a material having substantially the same rigidity as stainless steel. Preferably, each bar in the series is color coded or otherwise visually distinguished from bars having different stiffness characteristics.

Typical values for 8 mm. diameter rods which may be used in the apparatus of the invention are:

| Material | Average flexural modulus $\times 10^6$ psi |
| --- | --- |
| stainless steel (not X-ray translucent) | 28.0 |
| epoxy/carbon fiber (X-ray translucent) | 14.0 to 29.0 |
| epoxy/fiberglass (X-ray translucent) | 7.0–8.0 |

Preferably the body of the pin-to-bar clamp 3 also is made from an X-ray translucent material for the same reason as that of the rigid bar. A typical material in this case is a nylon/carbon fiber composite having a tensile strength of 24,000–32,000 p.s.i., preferably 28,000 p.s.i., and a flexural modulus of 2.0–2.4$\times 10^6$ p.s.i., preferably 2.2$\times 10^6$ p.s.i.

Details of the pin-to-bar clamp are illustrated in FIGS. 2–8 and 8A of the drawings.

The preferred pin-to-bar clamp, 3, comprises a body portion 4, of substantially C-shaped configuration having a first branch, 5, and a second branch, 6. Said first branch has an arm, 7, located at the terminus of the branch, which arm extends perpendicularly to the plane of the body portion and has two indents, 8, therein. A capture bar, 9, overlies said extending arm, 7, and is provided with two indents, 10, which are juxtaposed to the indents in the extending arm so that each pair of indents cooperates to accommodate an articulating ball, 11, holding a pin, 1.

The branches 5,6 of the body portion, together with a cooperating side indent, 12, in the capture bar, embrace in articulating ball, 13, which holds the rigid bar, 2.

Figures 9, 9A:
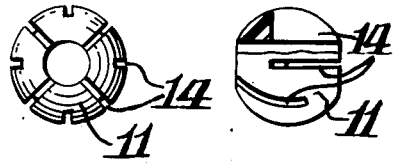
FIG. 9 is a plan view of an articulating ball.
FIG. 9A is a side view of said ball.

A typical articulating ball, 11 is illustrated in more detail in FIG. 9 and FIG. 9A. Said ball has an axial hole to accommodate a pin 1 and radial slots 14 which extend, alternately, over a major portion of the circumference (see FIG. 9A) to allow for compression and consequent locking of the pin when the locking means is tightened. The articulating ball for the rigid bar is of similar configuration but of larger size than the ball for each pin.

In the illustrated preferred embodiment the locking means comprises two threaded screws 15, 16 which terminate in thumbscrews, 17 and 18, respectively, and are adapted to be received in a threaded hole, 19, in the capture bar. Preferably the hole is provided with an aluminum or stainless steel insert for the threaded part. Said two screws act independently of each other allowing the pins and rigid bar to be locked in position separately.

Alternatively the locking means may be operated by a single screw passing through the first branch, capture bar and second branch, consecutively and adapted to be tightened through a thumb screw, wing nut or the like, but such alternative embodiment does not provide the flexibility of independant locking.

FIGS. 10 to 15 illustrate a bar-to-bar clamp according to the invention. Such clamp is preferably made from a rigid X-ray translucent material the same as the material used for the pin-to-bar clamp described above.

The preferred bar-to-bar clamp comprises a female component, 20, and a male component 21. The male component comprises a tapered projection, 22, adapted to be located in a cooperating indent, 23, in the female component. The projection and indent together form a taper lock which is rotatably adjustable and self centering. The taper lock is tightened by means of a screw, 24, which passes through a threaded hole in each of the components and is tightened and loosened with a terminal thumb screw, 25.

The male component contains a slot 26 and the female component a slot 27 each of which slots extends into a circular hole adapted to accommodate rigid bars, 2 and 2A. In the unlocked position the bars move freely in said holes and the taper lock may be rotated until the bars are located in the desired position to stabilize the bone under treatment. The thumb screw 25 is then tightened thus locking both rigid bars in the desired position. FIG. 15 illustrates a taper lock with two bars shown in parallel relationship for ease of illustration. In practice the bars would normally be at an angle to each other and the possible frame configurations that may be provided with this system include half frames, triangular frames (both transverse and bilateral) and bilateral frames using half pins and transfixing pins. The stiffness of the system may be varied by using rigid bars of different moduli. The stiffer bars would be used for early healing and the more flexible bars for late healing.

As stated above, in a modified embodiment of the invention, a clamp of the type identified herein as a bar-to-bar clamp may be used to couple a pin to a bar. In such embodiment either one of the circular holes will have a diameter adapted to accommodate an appropriate pin, rather than a bar. For example a clamp having two separable portions adjustably connected to each other through a taper lock may be adapted to couple a 3 mm. diameter pin to a 5 mm. diameter bar; a 5 mm. pin to an 8 mm. bar; or any other combination of pin to bar dimensions. Such embodiment may be used as the sole fixation apparatus in the case of simple fractures or in combination with any other arrangement of pins, bars and clamps as described herein.

It is to be understood that the dimensions of the pins, bars and clamps used in an apparatus according to the invention and the manner in which they are assembled with respect to each other and the fracture to be treated will depend upon the size of the bone and location of the fracture or fractures to be stabilized. Thus for large bones, for example the femur, a combination of 5 mm. pins and 8 mm. bars with appropriate size clamps normally would be suitable; while for smaller bones, e.g. the lower tibia, a combination of 3 mm. pins and 5 mm. bars would be suitable.

The apparatus illustrated in the drawings and described herein possesses numerous advantages and benefits, including:

Ease of application;
Simple adjustment, with few pieces and only two tightening screws for the simple pin-to-bar system;
Only one tightening screw for each bar-to-bar clamp in the modified framework system;
Lightweight;—greater patient acceptance due to less bulk;
The use of X-ray translucent materials facilitating examination of fractures;
Inexpensive—possibly disposable;
Provides greater access to fractures
Accommodates standard Hoffmann-type instrumentation;
Allows incremental increase in load sharing utilizing a compression distraction tool; and may be packed presterile.

I claim:

1. An apparatus for the external fixation and stabilization of a bone fracture, which comprises at least two pins adapted to pass through skin, flesh and bone on opposite sides of the fracture site; at least one first rigid bar having predetermined torsional, flexural and axial stiffness characteristics; at least two pin-to-bar clamps, each connecting at least one of said pins to said bar in a manner such that said clamps are translatable along said bar, the attachment of each of the pins to its associated clamp and of the bar to each clamp being each through an articulating ball which allows universal rotational adjustment of the pin or bar, respectively, each of said clamps comprising a body portion with a first branch connected to a second branch, an arm located at the terminus of said first branch, said arm extending perpendicularly to the plane of the body portion and having at least one indent, and a capture bar overlying said extending arm, wherein the branches of said body portion embrace the articulating ball which accommodates said rigid bar and the capture bar is provided with at least one indent which is juxtaposed to said indent in said extending arm so that said indents cooperate to accommodate each articulating ball holding a pin; and locking means for locking each pin to each clamp and each clamp to said rigid bar.

2. An apparatus according to claim 1, in which the body portion of each clamp is substantially C-shaped, said capture bar is located between the branches thereof with one end extending towards the crook of the C, and said end and said branches cooperate to embrace the articulating ball which accommodates said rigid bar.

3. An apparatus according to claim 2, in which said locking means comprises a first locking means for locking each pin to each clamp and independent second locking means for locking each clamp to said rigid bar.

4. An apparatus according to claim 3, in which the capture bar is provided with at least one first threaded socket on one side and a second threaded socket on the opposite side, said first locking means is at least one screw which passes through said extending arm and engages with said first threaded socket and said second locking means is a screw which passes through the second branch of the body portion and engages with said second threaded socket.

5. An apparatus according to claim 1, which comprises four pins arranged in two pairs, each pair attached to a single clamp, wherein the extending arm of each clamp extends on both sides of the first branch of the body portion.

6. An apparatus according to claim 1 which additionally includes at least one second rigid bar operatively attached to said first rigid bar through a bar-to-bar clamp comprising two separable portions adjustably connected to each other through a taper lock.

7. An apparatus according to claim 1, in which said first rigid bar and said clamps are made from X-ray translucent material.

8. An apparatus according to claim 7, in which the X-ray translucent material of said bar is an epoxy/carbon or epoxy/fiberglass composite, and the X-ray translucent material of said clamps is a nylon/carbon fiber composite.

9. An apparatus according to claim 1, in which said first rigid bar is one of a series of bars each made from a material having different torsional, flexural and axial stiffness characteristics from those of other members of the series, said bars being adapted to be interchanged in the apparatus to provide external fixation of diminishing stiffness as the healing of the fracture to which the apparatus is applied progresses.

10. An apparatus for the external fixation and enhanced stabilization of a bone fracture, which comprises at least two pins adapted to pass through skin, flesh and bone on opposite sides of the fracture site; at least one first rigid bar having predetermined torsional, flexural and axial stiffness characteristics; at least one second rigid bar having similar characteristics to said at least one first rigid bar; at least two pin-to-bar clamps and at least one bar-to-bar clamp, each of said pin-to-bar clamps connecting at least one of said pins to one of said rigid bars in a manner such that said clamps are translatable along said bar or bars, the attachment of each of the pins to its associated pin-to-bar clamp and of each bar to each pin-to-bar clamps being through an articulating ball which allows universal rotational adjustment of the pin or bar, respectively; each of said pin-to-bar clamps comprising a body portion with a first branch connected to a second branch and having an arm located at the terminus of said first branch, said arm extending perpendicularly to the plane of the body portion and having at least one indent; and a capture bar overlying said extending arm, wherein the branches of said body portion embrace the articulating ball which accommodates a rigid bar and the capture bar is provided with at least one indent which is juxtaposed to said indent in said extending arm so that said indents cooperate to accommodate each articulating ball holding a pin; and locking means for locking each pin to each pin-to-bar clamp and each pin-to-bar clamp to each rigid bar; each of said bar-to-bar clamps comprising two separable portions adjustably connected to each other through a taper lock.

11. An apparatus according to claim 10, in which said taper lock comprises a first substantially U-shaped member adapted to accommodate a first rigid bar within an aperture formed by the opposing legs of the U and located at the distal end of the member and having a male-tapered portion attached to the outside surface of one of the legs; a separate second substantially U-shaped member adapted to accommodate a second rigid bar in a manner similar to said first member, said second member having a female-tapered portion attached to the outside surface of one of its legs; said male and female tapered portions being adapted to co-operatively engage with each other; and locking means for locking said portions and said bars in a desired operative engagement with each other.

12. An apparatus according to claim 10, comprising at least two first rigid bars, each attached through said pin-to-bar clamps to at least two pins adapted to be affixed on opposite sides of said fracture site, with each pair of pins at an angle to the plane of each other pair of pins, said rigid bars being connected through bar-to-bar clamps to at least one second rigid bar in a manner such that the arrangement of first and second rigid bars forms a framework providing enhanced stability to the fractured bone.

13. An apparatus according to claim 10, in which each rigid bar and each clamp is made from X-ray translucent material.

14. An apparatus according to claim 13, in which the X-ray translucent material of said bars is an epoxy/carbon or epoxy/fiberglass composite, and the X-ray translucent material of said clamps is a nylon/carbon fiber composite.

15. An apparatus according to claim 10, in which each first rigid bar is one of a series of bars each made from a material having different torsional, flexural and axial stiffness characteristics from those of other members of the series, said bars being adapted to be interchanged in the apparatus to provide external fixation of diminishing stiffness as the healing of the fracture to which the apparatus is applied progresses.

16. A modified apparatus for the external fixation and stabilization of a bone fracture which comprises at least two pins adapted to pass through skin, flesh and bone and at least one rigid bar having predetermined torsional, flexural and axial stiffness characteristics, said pins being coupled to said at least one rigid bar through appropriate clamps, wherein at least one of the pins is coupled to a rigid bar through a clamp containing two separable portions adjustably connected to each other through a taper lock comprising a first substantially U-shaped member accommodating the pin within an aperture formed by the opposing legs of the U and located at the distal end of the member and having a male-tapered portion attached to the outside surface of one of the legs; a separate second substantially U-shaped member accommodating the rigid bar in a manner similar to said first member, said second member having a female-tapered portion attached to the outside surface of one of its legs; said male and female tapered portions being adapted to co-operatively engage with each other; and locking means for locking said portions and said pin and said bar in a desired operative engagement with each other.

* * * * *